United States Patent [19]

Chenard

[11] Patent Number: 5,338,754
[45] Date of Patent: Aug. 16, 1994

[54] 2-PYRROLIDINO-1-ALKANOL DERIVATIVES AS ANTIISCHEMIC AGENTS

[75] Inventor: Bertrand L. Chenard, Waterford, Conn.

[73] Assignee: Pfizer Inc, New York, N.Y.

[21] Appl. No.: 96,913

[22] Filed: Jul. 23, 1993

Related U.S. Application Data

[62] Division of Ser. No. 932,844, Aug. 20, 1992, Pat. No. 5,272,160, which is a division of Ser. No. 784,446, Oct. 23, 1991, Pat. No. 5,185,343.

[51] Int. Cl.$^5$ .................. A61K 31/40; C07D 207/12
[52] U.S. Cl. ......................... 514/422; 514/424; 548/517; 548/556
[58] Field of Search ........... 548/517, 556; 514/422, 514/424

[56] References Cited

U.S. PATENT DOCUMENTS

| | | | |
|---|---|---|---|
| 3,122,555 | 2/1964 | Janssen | 546/217 |
| 3,136,778 | 6/1984 | Cavalla et al. | 548/556 |
| 3,294,804 | 12/1966 | Carabateas | 546/218 |
| 3,462,444 | 8/1969 | Beckett | 546/216 |
| 3,509,164 | 4/1970 | Carron et al. | 546/241 |
| 4,393,069 | 7/1983 | Langbein et al. | 546/125 |

FOREIGN PATENT DOCUMENTS

| | | |
|---|---|---|
| 2546166 | 5/1983 | France . |
| 0202164 | 5/1986 | France . |
| 53-02474 | 1/1978 | Japan . |
| 53-59675 | 5/1978 | Japan . |

OTHER PUBLICATIONS

Carron, et al., Arzneim-Forsch. (Drug Res.), 21, 1992-9 (1971).
Gotti, et al., Journal of Pharmacology & Experimental Therapeutics, 247, 1211-22 (1988).
Carter, et al., Journal of pharmacology and Experimental Therapeutics, 247, 1222-32 (1988).

*Primary Examiner*—Bernard Dentz
*Attorney, Agent, or Firm*—Peter C. Richardson; Gregg C. Benson; Robert T. Ronau

[57] ABSTRACT

2-(8-Azabicyclo[3.2.1]oct-8-yl)alkanols of the formula

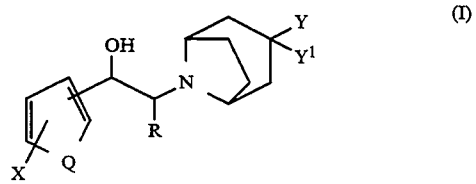

wherein Q is S or CH=CH; X is H, OH or another aromatic substituent; R is hydrogen, alkyl, alkenyl or alkynyl; Y and $Y^1$ are taken together and are arylmethylene or aralkylmethylene (or a corresponding epoxy derivative) or Y and $Y^1$ are taken separately and Y is hydrogen or OH, and $Y^1$ is aryl, aralkyl, arylthio, or aryloxy; and structurally related 2-(piperidino)alkanols; and 2-(pyriolidino)alkanols pharmaceutical compositions thereof; methods of treating CNS disorders therewith; and intermediates useful in the preparation of said compounds.

12 Claims, No Drawings

2-PYRROLIDINO-1-ALKANOL DERIVATIVES AS ANTIISCHEMIC AGENTS

This is a division, of co-pending application Ser. No. 07/932,844, filed on Aug. 20, 1992, now U.S. Pat. No. 5,272,169 entitled "2-Piperidino-1-Alkanol Derivatives as Antiischemic Agents," which is a division of application Ser. No. 07/784,446, filed on Oct. 23, 1991, now U.S. Pat. No. 5,785,393 entitled "2-Piperidino-1-Alkanol Derivatives as Antiischemic Agents," which is a continuation of International Application No. PCT/US90/00292, filed Jan. 16, 1990, entitled "2-Piperidino-1-Alkanol Derivatives as Antiischemic Agents," which is a continuation-in-part of copending International Application No. PCT/US89/02176, filed May 17, 1989, entitled "2-Piperidino-1-Alkanol Derivatives as Antiischemic Agents" (now abandoned).

BACKGROUND OF THE INVENTION

The present invention is directed to neuroprotective (antiischemic and excitory aminoacid receptor blocking) 2-piperidino-1-alkanol derivatives defined by the formulas (I), (II) and (III) below; pharmaceutically acceptable salts thereof; a method of using these compounds in the treatment of stroke or CNS degenerative diseases such as Alzheimer's disease, Huntington's disease and Parkinson's disease; and to certain intermediates therefor.

Ifenprodil is a racemic, so-called dl-erythro compound having the relative stereochemical formula

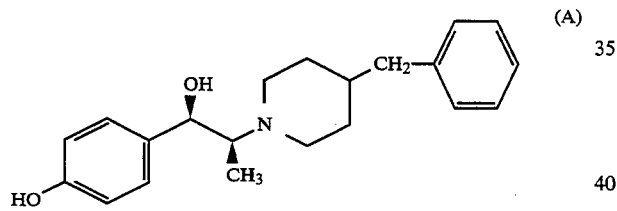

(A)

which is marketed as a hypotensive agent, a utility shared by a number of close analogs; Carron et al., U.S. Pat. No. 3,509,164; Carton et al., Drug Res., v. 21, pp. 1992-1999 (1971). More recently, ifenprodil has been shown to possess antiischemic and excitory aminoacid receptor blocking activity; Gotti et al., J. Pharm. Exp. Therap., v. 247, pp. 1211-21 (1988); Carter et al., loc. cit., pp. 1222-32 (1988). See also French Patent 2546166. A goal, substantially met by the present invention, has been to find compounds possessing such neuroprotective effect in good measure, while at the same time having lowered or no significant hypotensive effect.

Certain structurally related 1-phenyl-3-(4-aryl-4-acyloxypiperidino)-1-propanols have also been reported to be useful as analgesics, U.S. Pat. No. 3,294,804; and 1-[4-(amino- and hydroxy-alkyl)phenyl]-2-(4-hydroxy-4-tolylpiperazino)-1-alkanols and alkanones have been reported to possess analgesic, antihypertensive, psychotropic or antiinflammatory activity, Japanese Kokai 53-02,474 (CA 89:43498y; Derwent Abs. 14858A) and 53-59,675 (CA 89:146938w; Derwent Abs. 48671A).

SUMMARY OF THE INVENTION

The present invention is directed to compounds of the formula

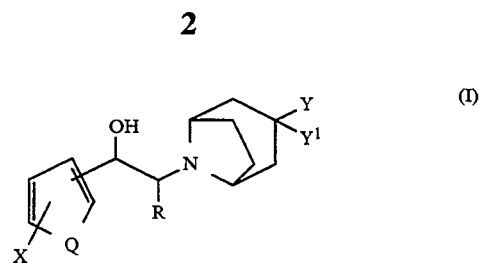

(I)

wherein

R is H, $(C_1-C_6)$alkyl, $(C_2-C_6)$alkenyl or $(C_2-C_6)$alkynyl;

X is hydrogen, $(C_1-C_3)$alkyl, halo, $OR^1$, $OCOR^1$, $CO_2R^1$, $SR^1$, $NHR^1$, $NHCOR^1$, $CONH_2$ or CN;

$R^1$ is hydrogen or $(C_1-C_3)$alkyl;

Q is S or CH=CH;

Y and $Y^1$ are taken together and are

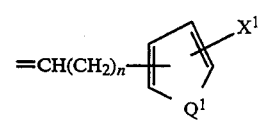

or

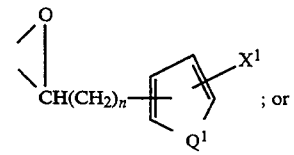

; or

Y and $Y^1$ are taken separately, and

Y is hydrogen or OH, and $Y^1$ is

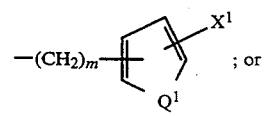

; or

Y is hydrogen and $Y^1$ is

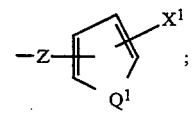

;

n is 0, 1, 2 or 3;

m is 0, 1, 2, 3 or 4;

$Q^1$ is independently a value of Q as defined above;

$X^1$ is independently a value of X as defined above; and

Z is O, S, SO or $SO_2$; compounds of the formula

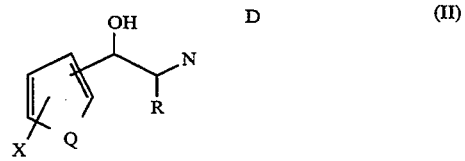

(II)

wherein

D is

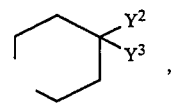,

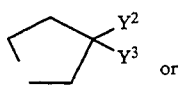 or

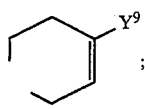;

$Y^2$ and $Y^3$ are taken together and are

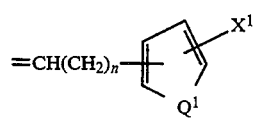

or

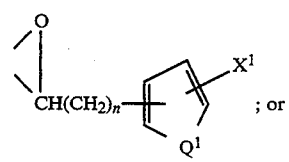; or $Y^2$ and $Y^3$ are taken separately, and $Y^2$ is OH and $Y^3$ is

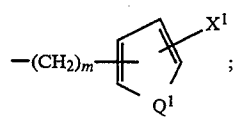;

$Y^9$ is

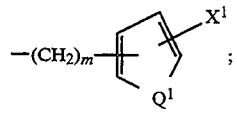;

and R, $R^1$, X, $X^1Q^1$, $Q^1$, n and m are as defined above; and compounds of the formula

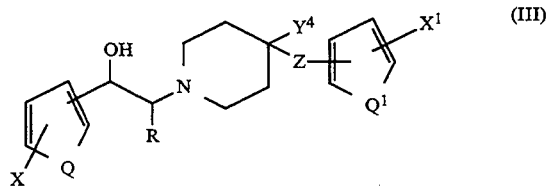 (III)

wherein
$Y^4$ is H; and
R, $R^1$, Q, $Q^1$, X, $X^1$ and Z are as defined above; and the pharmaceutically acceptable acid addition salts of these compounds.

The expression "pharmaceutically acceptable acid addition salts" is intended to include but is not limited to such salts as the hydrochloride, hydrobromide, hydroiodide, nitrate, hydrogen sulfate, dihydrogen phosphate, mesylate, maleate, and succinate. Such salts are conventionally prepared by reacting the free base form of the compound (I), (II) or (III) with an appropriate acid, usually one molar equivalent, and in a solvent. Those salts which do not precipitate directly are generally isolated by concentration of the solvent and/or addition of a non-solvent.

The preferred compounds of the present invention generally have R as methyl and possess 1S*,2S* or threo relative stereochemistry at the 1- and 2-positions of the propanol chain, i.e.,

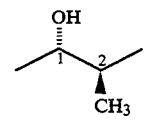

Furthermore, regardless of the value of R, preferred compounds of the present invention are of the formula (I) or (II) having Y and $Y^1$ or $Y^2$ and $Y^3$ taken separately, further having Y or $Y^2$ as OH, or $Y^1$ as $—Z(C_4H_3Q^1)X^1$; or are of the formula (III). The preferred value of Z in all cases is S.

The present invention is also directed to pharmaceutical compositions and to methods of treating a mammal, particularly man, suffering a central nervous disorder, which comprises administering to said mammal a neuroprotective effective amount of a compound of the formula (I), (II) or (III). Said compositions and methods are particularly valuable in the treatment of stroke, Alzheimer's disease, Parkinson's disease, Huntington's disease and related disorders of the central nervous system.

The present invention is further directed to intermediate compounds of the formula

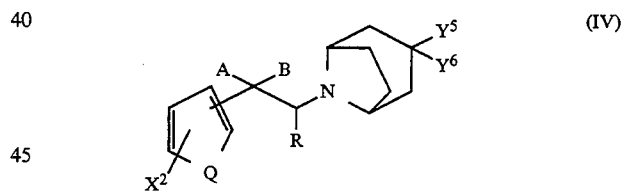 (IV)

wherein
A and B are taken together and are oxygen, forming, together with the carbon to which they are attached a carbonyl group, or A and B are taken separately and A is hydrogen and B is hydroxy;
$X^2$ is hydrogen, $(C_1-C_3)$alkyl, halo, $OR^1$, $OR^2$, $COOR^1$, $OCOR^1$, $SR^1$, $SR^2$, $NHR^1$, $NR^1R^3$, $NHCOR^1$, $CONH_2$ or CN;
$R^1$ is hydrogen or $(C_1-C_3)$alkyl;
$R^2$ is a conventional hydroxy or mercaptan protecting group;
$R^3$ is a conventional amino protecting group;
$Y^5$ and $Y^6$ are taken together and are

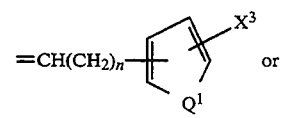 or

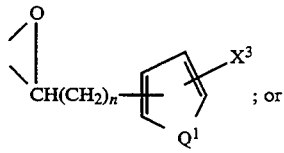 ; or $Y^5$ and $Y^6$ are taken separately and $Y^5$ is hydrogen or OH, and $Y^6$ is

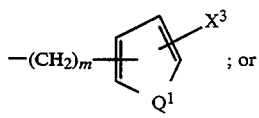 ; or $Y^5$ is hydrogen and $Y^6$ is

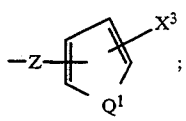 ;

$X^3$ is independently a value of $X^2$ as defined above; with the proviso that when A and B are taken separately, at least one of $X^2$ and $X^3$ is $OR^2$, $SR^2$ or $NR^1R^3$;

Z is O, S, SO or $SO_2$; and

R, Q, $Q^1$, n and m are as defined above; intermediate compounds of the formula

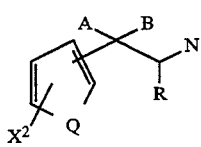 (V)

wherein
E is

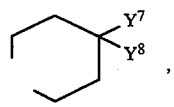,

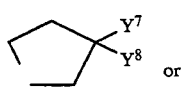 or

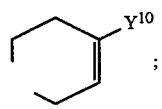 ;

$Y^7$ and $Y^8$ are taken together and are

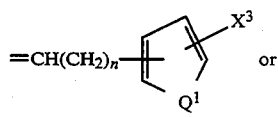 or

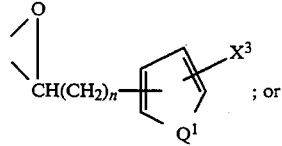 ; or $Y^7$ and $Y^8$ are taken separately, and $Y^7$ is OH and $Y^8$ is

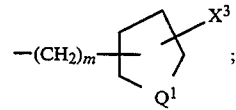 ;

$Y^{10}$ is

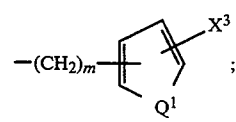 ;

and A, B, R, $R^1$, $R^2$, $R^3$, Q, $Q^1$, $X^2$, $X^3$, n and m are as defined above, with the same proviso concerning A and B; and intermediate compounds of the formula

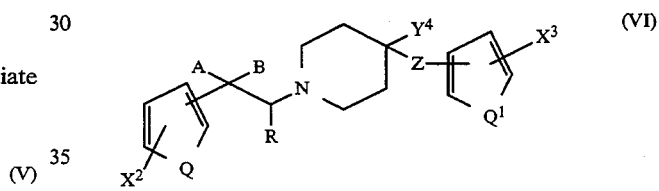 (VI)

wherein all groups are defined as above, with the same proviso concerning A and B.

Those compounds of the formula (I) or (IV) specified as endo have the hydroxy group or oxirane oxygen on the same side of the piperidine ring as the ethylene bridge.

It will be noted that those compounds of the formula (I) to (VI) which are 1-alkanols possess an asymmetric C-1 carbon, while those wherein R is other than hydrogen possess a second asymmetric center at the C-2 carbon of the alkanol. Similarly, in those compounds of the formulas (IV) to (VI) which are 1-alkanones wherein R is other than hydrogen possess a C-2 asymmetric carbon. It will be evident to those skilled in the art of organic chemistry, therefore, that such compounds can be resolved into optical isomers showing equal but opposite rotation of plane polarized light. For example, all of these compounds are potentially resolved by fractional crystallization of their diastereomeric addition salts with an optically active acid, as exemplified below; while the alcohols are also potentially resolved by chromatography or fractional crystallization of esters derived by reaction with activated forms of optically active acids or with optically active isocyanates. Alternatively, optically active forms of certain of the present compounds are obtained by reaction of an appropriate amine with an optically active epoxide, as also exemplified below. Thus, the present invention should not be construed as limited to the racemic forms of the present compounds.

DETAILED DESCRIPTION OF THE INVENTION

The compounds of the present invention, having the formula (I), (II) and (III) defined above, are readily and generally prepared by nucleophilic displacement followed by reduction of the resulting ketone to alcohol as detailed below.

The precursor ketones are generally initially prepared with —OH, —SH and —NHR$^1$ groups in protected form, i.e., as —OR$^2$, —SR$^2$ or —NR$^1$R$^3$ groups in the compounds of the formulas (IV), (V) and (VI) where A and B are taken together as oxygen to form a carbonyl group. Such protected ketones are generally formed by nucleophilic displacement of an appropriately substituted 2-halo, 2-alkanesulfonyloxy- or 2-arylsulfonyloxy-1-alkanone with an appropriately substituted piperidine derivative, e.g.,

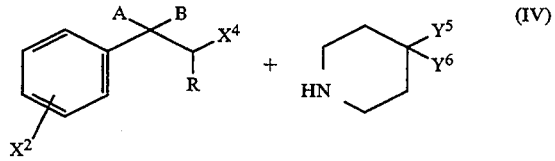 (IV)

wherein X$^4$ is typically chloro, bromo, mesyloxy or tosyloxy. This reaction is carried out under conditions typical of nucleophilic displacements in general. Where the two reactants are about equivalent in availability, close to substantially molar equivalents may be used; although when one is more readily available, it is usually preferred to use that one in excess, in order to force this bimolecular reaction to completion in a shorter period of time. The reaction is generally carried out in the presence of at least 1 molar equivalent of a base, the piperidine derivative itself, if it is readily available, but more usually a tertiary amine which is at least comparable in base strength to the nucleophilic piperidine; and in a reaction inert solvent such as ethanol. If desired, the reaction is catalyzed by the addition of up to one molar equivalent or more of an iodide salt (e.g., NaI, KI). Temperature is not critical, but will generally be somewhat elevated in order to force the reaction to completion within a shorter time period, but not so high as to lead to undue decomposition. A temperature in the range of 50°-120° C. is generally satisfactory. Conveniently, the temperature is the reflux temperature of the reaction mixture.

As used in the preceding paragraph, and elsewhere herein, the expression "reaction inert solvent" refers to any solvent which does not interact with starting materials, reagents, intermediates or products in a manner which adversely affects the yield of the desired product.

If desired, those ketone intermediates having SH or NHR$^1$ groups in protected form (OR$^2$, SR$^2$ or NR$^1$R$^3$) can be deprotected at this stage by conventional methods. For example, when R$^2$ is triisopropylsilyl or tert-butyldimethylsilyl, the protecting group is conveniently removed by reaction with tetrabutylammonium fluoride (generally, substantially 2 molar equivalents) in a reaction inert solvent such as tetrahydrofuran. When R$^2$ is benzyl or R$^3$ is benzyloxycarbonyl, the protecting group will generally be removed by conventional hydrogenolysis over a noble metal catalyst in a reaction inert solvent, e.g., using 10% Pd/C as catalyst, preferably at low pressures (e.g., 1-10 atmospheres) and temperatures (e.g., 20°-75° C.) and generally in a reaction inert solvent such as methanol.

Generally excluding ketone intermediates containing ester groups or protecting groups such as benzyloxycarbonyl (which will generally be removed prior to ketone reduction), but otherwise with or without prior removal of protecting groups, the ketone intermediates are conveniently converted to corresponding alcohols by conventional reduction with a LiAlH$_4$, usually in excess (e.g., tool for tool), in a reaction inert solvent such as tetrahydrofuran at reduced temperature (e.g., −15° C. to 15° C.). Alternatively, ketone intermediates, particularly those containing ester groups, are reduced with a milder hydride reducing agent such as NaBH$_4$, again usually in excess, now in a protic solvent such as methanol or ethanol, generally at somewhat higher temperature, e.g., 15°-45° C.

Any protecting groups which are still in place after ketone reduction are then removed according to the methods described above. Certain other transformations, such as olefin hydrogenation, epoxidation and sodium/liquid NH$_3$ reduction of epoxides, e.g.,

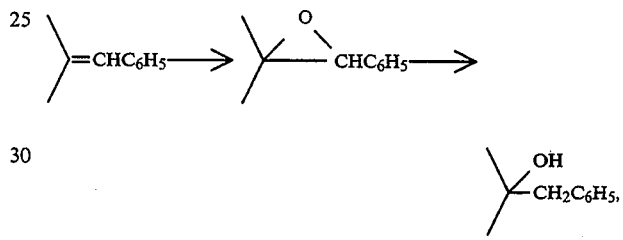

are also optionally carried out late in the synthetic sequence, e.g., after coupling to form ketone, after removal of protecting groups (so long as the unprotected groups do not interfere with the transformations) and/or after reduction of ketone to alcohol.

Said epoxidations are readily accomplished, for example, by reacting a methylene compound with substantially one molar equivalent of m-chloroperbenzoic acid in a reaction inert solvent such as CH$_2$Cl$_2$. The reduction of epoxide to alcohol is readily accomplished by conventional sodium/liquid ammonia, generally carried out at temperatures below the boiling point of liquid NH$_3$ (e.g., at −78° C., the temperature of an acetone-dry ice bath) in the presence of a reaction inert solvent such as tetrahydrofuran.

The starting materials and reagents required for the synthesis of the compounds of the present invention are readily available, either commercially, according to literature methods, or by methods exemplified in Preparations below.

The present compounds of the formula (I), (II) and (III) possess selective neuroprotective activity, based upon their antiischemic activity and ability to block excitory aminoacid receptors, while at the same time generally having lowered or no significant hypotensive activity. The antiischemic activity of the present compounds is determined according to one or more of the methods which have been detailed previously by Gotti et al. and Carter et al. cited above, or by similar methods. The ability of the compounds of the present invention to block excitatory amino acid receptors is demonstrated by their ability to block N-methyl-D-aspartic acid-induced (NMDA) elevations of cGMP in neonatal rat cerebellums according to the following procedure.

Cerebellums from ten 8–14 day old Wistar rats are quickly excised and placed in 4° C. Krebs/bicarbonate buffer, pH 7.4 and then chopped in 0.5 mm×0.5 mm sections using a McIlvain tissue chopper (The Nickle Laboratory Engineering Co., Gomshall, Surrey, England). The resulting pieces of cerebellum are transferred to 100 ml of Krebs/bicarbonate buffer at 37° C. which is continuously equilibrated with 95:5 $O_2/CO_2$. The pieces of cerebellum are incubated in such a manner for ninety minutes with three changes of the buffer. The buffer then is decanted, the tissue centrifuged (1 min., 3200 r.p.m.) and the tissue resuspended in 20 ml of the Krebs/bicarbonate buffer. Then, 250 $\mu$l aliquots (approximately 2 mg) are removed and placed in 1.5 ml microfuge tubes. To those tubes are added 10 $\mu$l of the compound under study from a stock solution followed, after a 10 minute incubation period, by 10 $\mu$l of a 2.5 mM solution of NMDA to start the reaction. The final NMDA concentration is 100 $\mu$M. Controls do not have NMDA added. The tubes are incubated for one minute at 37° C. in a shaking water bath and then 750 $\mu$l of a 50 mM Tris-Cl, 5 mM EDTA solution is added to stop the reaction. The tubes are placed immediately in a boiling water bath for five minutes. The contents of each tube then are sonicated for 15 seconds using a probe sonicator set at power level three. Ten microliters are removed and the protein determined by the method of Lowry, Anal. Biochem. 100:201–220 (1979). The tubes are then centrifuged (5 min., 10,000 xg), 100 $\mu$l of the supernatant is removed and the level of cyclic GMP (cGMP) is assayed using a New England Nuclear (Boston, Mass.) cGMP RIA assay according to the method of the supplier. The data is reported as pmole cGMP generated per mg. protein. Undesired hypotensive activity is also determined by known methods, for example, according to the methods of Carron et al., also cited above.

Such selective neuroprotective antiischemic and excitatory amino acid blocking activities reflect the valuable utility of the present compounds in the treatment of degenerative CNS (central nervous system) disorders such as stroke; and Alzheimer's disease, Parkinson's disease and Huntington's disease; without significant potential for concurrent undue drop in blood pressure. In the systemic treatment of such diseases with a neuroprotective amount of compounds of the formula (I), (II) or (III), the dosage is typically from about 0.02 to 10 mg/kg/day (1–500 mg/day in a typical human weighing 50 kg) in single or divided doses, regardless of the route of administration. Of course, depending upon the exact compound and the exact nature of the individual illness, doses outside this range may be prescribed by the attending physician. The oral route of administration is generally preferred. However, if the patient is unable to swallow, or oral absorption is otherwise impaired, the preferred route of administration will be parenteral (i.m., i.v.) or topical.

The compounds of the present invention are generally administered in the form of pharmaceutical compositions comprising at least one of the compounds of the formula (I), (II) or (III), together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; for parenteral administration, in the form of injectable solutions or suspensions, and the like; and for topical administration, in the form of solutions, lotions, ointments, salves and the like.

The present invention is illustrated by the following examples, but is not limited to the details thereof.

All non-aqueous reactions were run under nitrogen for convenience and generally to maximize yields. All solvents/diluents were dried according to standard published procedures or purchased in a predried form. All reactions were stirred either magnetically or mechanically. NMR spectra are recorded at 300 MHz and are reported in ppm. The NMR solvent was $CDCl_3$ unless otherwise specified. IR spectra are reported in $cm^{-1}$, generally specifying only strong signals.

EXAMPLE 1

2-(3-Phenylmethylene-8-azabicyclo[3.2.1]oct-8-yl)-1-(4-(triisopropylsilyloxy)phenyl)-1-propanone A mixture of 3-phenylmethylene-8-azabicyclo[3.2.1]octane (1.09 g, 4.87 mmol), 4-(triisopropylsilyloxy-alpha-bromopropiophenone (1.88 g, 4.88 mmol) and triethylamine (1.5 ml, 10.76 mmol) in ethanol (75 ml) was refluxed 22 hours. After cooling, ether (50 ml) was added and the mixture was filtered through diatomaceous earth. The filtrate was concentrated and chromatographed on silica gel (2×6 inches, hexane then ethyl acetate/hexane gradient) to give 0.56 g (23%) of an orange oil product; NMR 8.18 (d, 2H), 7.25 (t, 2H), 7.12 (d, 3H), 6.86 (d, 2H), 6.29 (s, 1H), 4.08 (m, 1H), 3.47–3.26 (m, 2H), 2.75 (m, 1H), 2.57–2.37 (m, 2H), 2.03–1.72 (m, 4H), 1.6 (m, 1H; partially under water peak from NMR solvent), 1.40 (d, 3H), 1.25 (m, 3H), 1.09 (d, 18H).

EXAMPLE 2

Mixture of (1R*,2S*)- and (1S*,2S*)-2-(3-phenylmethylene-8-azabicyclo[3.2.1]oct-8-yl)-1-(4-(triisopropylsilyloxy)phenyl)-1-propanol To a slurry of $LiAlH_4$ (0.61 g, 16.07 mmol) in tetrahydrofuran (50 ml) at 0° C. was added title product of the preceding Example (8.04 g, 15.96 mmol) in tetrahydrofuran (150 ml) over 15 minutes. The mixture was stirred 15.5 hours at room temperature, then carefully quenched with water (1.2 ml), filtered over diatomaceous earth and concentrated to give a yellow oil (7.15 g, 89%). This mixture of racemic title products was used directly in the next reaction without purification.

EXAMPLE 3

(1S*,2S*)- and (1R*,2S*)-1-(4-hydroxyphenyl)-2-(3-phenyl-2-(3-phenylmethylene-8-azabicyclo[3.2.1]oct-8-yl)-1-propanol Title product of the preceding Example (7.15 g, 14.14 mmol) was dissolved in tetrahydrofuran (250 mo) and tetrabutylammonium fluoride (28.5 ml, 28.5 mmol, 1M in tetrahydrofuran) was added all at once. The solution was stirred at room temperature 18 hours, then concentrated and chromatographed on silica gel (4×6 inches, ethyl acetate/hexane gradient followed by methanol-/ethyl acetate gradient) to give first the racemic (1S*,2S*)-title product (1.58 g) followed by the more polar racemic (1R*,2S*)-title product (2.88 g). (Note that because of the asymmetry in the 3-phenylmethylene-8-azabicyclo[3.2.1]oct-8-yl side chain, each of these products is actually a mixture of two racemates).

The (1S*,2S*)-product was recrystallized from ethyl acetate/hexane to give 0.923 g of white solid; mp 175°–177° C.; NMR includes 4.10 (t, J=7.7 Hz, 1H); Anal. C 78.77, H 7.90, N 3.92, calcd. C 79.05, H 7.90, N 3.92.

The (1R*,2S*)-product was further purified by radial chromatography with 60% ethyl acetate/hexane elution to give 0.24 g of colorless oil. This oil was crystallized from ether/hexane to give 0.17 g of fluffy solid, mp 78.5°–85° C. The latter was converted to its HCl salt by bubbling HCl gas into an ether solution of the compound for 3 minutes. The white precipitate was collected and recrystallized from ethanol to yield the (1R*,2S*)-hydrochloride salt as its half hydrate; mp 215°–218° C.; NMR (DMSO-$d_6$) includes 5.17 (s, 1H) and 4.60–3.93 (m, 2H); Anal. C 70.00, H 7.45, N 3.35, calcd. for ½ $H_2O$ C 69.95, H 7.40, N 3.54.

EXAMPLE 4

2-(4-(Phenylthio)piperidino)-1-(4-(tert-butyldimethylsilyloxy)phenyl)-1-propanone This product was prepared according to the procedure of Example 1 using 4-phenylthiopiperidine (1.13 g, 5.85 mmol), triethylamine (0.82 ml, 5.88 mmol), and 4-(tert-butyldimethylsilyloxy)-alpha-bromo-propiophenone (2.0 g, 5.83 mmol) and a reflux time of 21.5 hours. The product was isolated by silica gel flash chromatography with an ethyl acetate/hexane gradient elution. The yield was 1.29 g of title product as a yellow oil: NMR 8.00 (d, J=9 Hz, 7.35 (d, J=7.8 Hz, 2H), 7.25 (m, 3H), 6.81 (d, J=8.4 Hz, 2H), 4.00 (q, J=6.8 Hz, 1H), 3.03 (m, 1H), 2.91–2.87 (m, 1H), 2.80–2.76 (m, 1H), 2.44 (dt, J=9.5, 2.6 Hz, 1H), 2.29–2.19 (m, 1H), 1.93–1.85 (m, 2H), 1.66–1.52 (m, 2H-partially under water peak from solvent), 1.22 (d, J=7.1 Hz, 3H), 0.97 (s, 9H), 0.22 (s, 6H). Later fractions from the chromatography yielded an additional 0.51 g of product which had desilylated during the reaction. This material could also be converted to the final targeted compounds by procedures below.

By the same methods 4-(triisopropylsilyloxy)-alpha-bromopropiophenone (9.97 g, 25.9 mmol) was converted to chromatographed 2-(4-(phenylthio)-piperidino)-1-(4-(triisopropylsilyloxy)phenyl)-1-propanone as a light orange oil: 8.32 g; NMR 8.00 (d, J=8.8 Hz, 2H), 7.37 (dd, J=1.5, 8.4 Hz, 2H), 7.29–7.18 (m, 3H), 6.86 (d, J=8.8 Hz, 2H), 4.02 (q, J=6.8 Hz, 3.08–3.00 (m, 1H), 2.85 (d, J=26.2 Hz, 1H), 2.75 (d, J=16.6 Hz, 1H), 2.45 (dt, J=11, 2.6 Hz, 1H), 2.23 (dt, J=9.8, 2.5 Hz, 1H), 1.96–1.88 (m, 2H), 1.71–1.50 (m, 5H), 1.09 (d, J=7 Hz, 18H).

EXAMPLE 5

(1S*,2S*)- and (1R*,2S*)-2-(4-Phenylthio)piperdino)-1(4-(triisopropylsilyloxy)phenyl)-1-propanol By the method of Example 2, the triisopropylsilyloxy product of the preceding Example (8.32 g, 16.7 mmol), using chromatography on silica gel with ethyl acetate/-hexane gradient elution to separate the isomers, was converted to 6.06 g of less polar (1S*, 2S*)-title product as an oil; NMR 7.41 (d, J=6.7 Hz, 2H), 7.32–7.24 (m, 3H), 7.15 (d, J=8.5 Hz, 2H), 6.82 (d, J=8.4 Hz, 2H), 4.14 (d, J=9.7 Hz, 1H), 3.11 (m, 1H), 2.88 (m, 1H), 2.69 (m, 1H), 2.69–2.55 (m, 2H), 2.21 (t, 1H), 2.03 (m, 2H), 1.85–1.58 (m, 3H), 1.35–1.20 (m, 2H), 1.23 (d, J=15 Hz, 18H), 1.07 (d, J=7 Hz, 3H); and to 0.2 g of more polar (1R*,2S*)-title product; NMR 7.35 (d, J=7 Hz, 2H), 7.28–7.16 (m, 3H), 7.08 (d, J=9 Hz, 2H), 6.78 (d, J=9 Hz, 2H), 4.68 (d, J=5 Hz, 1H), 3.10–2.98 (m, 1H), 2.98–2.87 (m, 1H), 2.75–2.60 (m, m, 2H), 2.33 (t, J=9 Hz, 1H), 2.16 (t, J=11 Hz, 1H), 1.91 (t, J=15 Hz, 2H), 1.70–1.48 (m, 2H), 1.32–1.12 (m, 4H), 1.06 (d, J=9 Hz, 18H), 0.88–0.78 (m, 3H).

EXAMPLE 6

(1S*,2S*)-1-(4-Hydroxyphenyl)-2-(4-(phenylthio)-piperidino)-1-propanol

Method A

To a slurry of $LiAlH_4$ (0.11 g, 2.9 mmol) in tetrahydrofuran (25 ml) chilled to 0° C. was added title product of Example 4 (1.29 g, 2.83 mmol) in tetrahydrofuran (50 ml). The reaction was warmed to ambient temperature for 2 hours, refluxed for 3 hours, and left to stir for 72 hours. The mixture was carefully quenched with water and filtered through diatomaceous earth. The filtrate was concentrated to a wet solid, which was taken up in ethyl acetate and washed with brine, dried ($CaSO_4$), concentrated to afford 0.41 g of white solid, and recrystallized from ether/hexane to give 0.16 g of title product; mp 155°–157° C.; NMR includes 4.12 (d, 1H); Anal. C 69.57, H 7.28, N 3.95, calcd. C 69.94, H 7.34, N 4.08. The alumina salts from the reaction were Sohxlet extracted with ethyl acetate for 24 hours. Concentration gave an additional 0.3 g of product.

Method B

The same product is obtained from the (1S*, 2S*)-title product of the preceding Example by the method of Example 3.

EXAMPLE 7

(1R*,2S*)-1-(4-Hydroxyphenyl)-2-(4-(phenylthio)-piperidino)-1-propanol

Following the procedure of Example 3, present title product was obtained from the (1R*,2S*)-title of Example 5 (0.2 g, 0.4 mmol) and tetrabutylammonium fluoride (0.8 ml, 0.8 mmol: 1M in tetrahydrofuran) tetrahydrofuran (5 ml) at ambient temperature for 72 hours. The product was obtained by silica gel flash chromatography (6×1 inches, ethyl acetate/hexane gradient elution) to give 0.14 g of semi-solid. Recrystallization from methylene chloride/hexane gave 0.056 g of white solid; mp 124.5°–126° C.; NMR includes 4.72 (d, J=4.1 Hz, 1H); Anal. C 69.68, H 7.24, N 4.14, calcd. C 69.94, H 7.34, N 4.08.

EXAMPLE 8

(1S*,2S*)-1-(4-Hydroxyphenyl)-2-(4-(phenylsulfonyl)-piperidino)-1-propanol

Title product of Example 6 (0.13 g, 0.378 mmol) was dissolved in $CH_2Cl_2$ (20 ml) and m-chloroperoxybenzoic acid (0.23 g, 1.133 mmol) was added all at once. The solution was stirred 23 hours, then the precipitated material was filtered to give 0.154 g of white solid which was the crude intermediate N-oxide. The latter was hydrogenated in a Parr apparatus in methanol (20 ml) with 10% palladium on carbon catalyst (0.03 g) at 50 psig hydrogen. The reaction was complete in 6 hours and was filtered through diatomaceous and concentrated to leave 0.166 g of yellow oil. This oil was taken up in $CH_2Cl_2$ and washed with saturated sodium bicarbonate. The organic phase was dried ($MgSO_4$) and concentrated to give 0.106 g of yellow oil, which was crystallized from ethyl acetate/hexane to yield 0.076 g of white solid; mp 169°–175° C. A portion of the product (0.045–0.050 g) was further purified by mixing vigorously with saturated sodium bicarbonate and ethyl acetate for 15 minutes. The phases were separated and the aqueous was further extracted with ethyl acetate (2x). The combined organic phase was dried ($CaSO_4$), concentrated to give a colorless oil, and crystallized from ethyl acetate to give 0.02 g of white powder; mp 195°–196° C.; NMR 7.88 includes 4.15 (d, J=9.7 Hz, 1H); Anal. C 63.77, H 6.61, N 3.61, calcd. C 63.98, H 6.71, N 3.73.

EXAMPLE 9

(1S*,2S*)-1-(4-Hydroxyphenyl)-2-(4-(phenylsulfinyl)-piperidino)-1-propanol

Title product of Example 6 (0.5 g, 1.46 mmol) was dissolved in $CH_2Cl_2$ (40 ml) and m-chloroperoxybenzoic acid (0.3 g, 1.48 mmol) was added all at once. After stirring overnight at ambient temperature, the mixture was concentrated directly onto silica gel and flash chromatographed (6×1 inches, ethyl acetate/hexane gradient) to give 0.34 g of crude product as a white solid which was further purified by partitioning between saturated $NaHCO_3$ and ethyl acetate with vigorous stirring for 20 minutes. The phases were separated and the organic layer was concentrated to leave a greasy solid which was crystallized from ethyl acetate/hexane to give 0.122 g of white solid; mp 110° C.; NMR includes 4.16 (long range coupled d, J=9.7 Hz, 1H); HRMS 360.1635, calcd. 360.1626.

EXAMPLE 10

1-(4-(Benzyloxy)phenyl)-2-(4-benzyl-4-hydroxypiperidino)-1-propanone

This product was prepared following the procedure of Example 1 from 4-hydroxy-4-benzylpiperidine (2.0 g, 10.46 mmol), triethylamine (1.46 ml, 10.47 mmol), and 4-benzyloxy-alpha-bromopropiophenone (3.33 g, 10.4 3 mmol) in ethanol (50 ml) with a reflux period of 24 hours. The present racemic product was obtained after silica gel flash chromatography with ethyl acetate/hexane gradient elution. The yield was 2.88 g (64%) of a yellow solid; NMR 8.06 (d, 2H), 7.52–7.08 (m, 10H), 6.97 (d, 2H), 5.11 (s, 2H), 4.00 (q, 1H), 2.72 (s, 2H), 2.72–2.53 (m, 2H), 2.43 (t, 1H), 1.85–1.39 (m, 6H), 1.23 (d, 3H). HRMS 412.2348, calcd. (—OH) 412.2273.

EXAMPLE 11

(1S*,2S*)-1-(4-(Benzyloxy)phenyl)-2-(4-benzyl-4-hydroxypiperidino)-1-propanol $NaBH_4$ (0.25 g, 6.61 mmol) was added all at once to a solution of title product of the preceding Example (2.88 g, 6.70 mmol) in ethanol (50 ml). The mixture was stirred 20 hours at ambient temperature as a precipitate formed. The solid was filtered and dried to yield 0.60 g of present title product; mp 147°–148° C.; NMR includes 4.17 (d, J=10 Hz, 1H); IR (KBr) 3387, 3024, 2936, 2909, 1611, 1513, 1453, 1239, 1026, 1011, 695. The filtrate from the above reaction was concentrated, the residue partitioned between ethyl acetate and water and the phases separated. The aqueous phase was extracted with ethyl acetate. The combined organic phases were washed with water, dried ($CaSO_4$) and concentrated to give 2.82 g of additional title product.

EXAMPLE 12

(1S*,2S*)-1-(4-Hydroxyphenyl)-2-(4-benzyl-4-hydroxypiperidino)-1-propanol

Title product of the preceding Example (0.49 g, 1.14 mmol) and tetrahydrofuran (30 ml) was chilled to −78° C. and ammonia gas (30 ml) was condensed into the mixture. Sodium (0. 082 g, 3.57 mmol) was added in four pieces. The reaction, which gradually turned blue, was stirred 15 minutes and then quenched with ammonium chloride (0.29 g). The reaction was allowed to warm to ambient temperature, with the ammonia boiling off. The reaction was concentrated and the residue was taken up in ethyl acetate and washed with water and brine. The organic phase was dried ($CaSO_4$) and concentrated to give 0.39 g of white solid. Recrystallization from hexane gave 0.19 g of present title product; NMR (DMSO-$d_6$) 7.25–7.11 (m, 5H), 7.08 (d, J=8.2 Hz, 2H), 6.68 (d, J=8.6Hz, 2H), 4.14 (s, 1H), 4.09 (d, J=9.2 Hz, 1H), 3.33 (s, 2H), 3.30 (s, 1H), 2.74 (m, 1H-partially under water peak from the NMR solvent), 2.60–2.35 (m, 4H-partially under NMR solvent peak), 1.70–1.44 (m, 4H), 0.63 (d, J=6.7 Hz, 3H). Deuterium oxide washed out the singlets at 4.14 and 3.30 ppm.

This product was recrystallized from ethyl acetate to give purified title product; mp 213°–214° C.; IR (KBr) 3263, 3023, 2940, 2917, 1615, 1517, 1453, 1273, 1221, 1186, 1020, 1011, 831, 687. Anal. C 73.73, H 8.03, N 4.01, calcd. C 73.87, H 7.97, N 4.10.

EXAMPLE 13

1-(4-(tert-Butyldimethylsilyloxy)phenyl)-2-(3-phenylthio-8-azabicyclo[3.2.1]oct-8-yl)-1-propanone Following the procedure of Example 1, this product was prepared from 4-tert-butyldimethylsilyloxy-alpha-bromopropiophenone (1.25 g, 3.65 mmol), 3-phenylthio-8-azabicyclo[3.2.1]octane (0.8 g, 3.65 mmol), and triethylamine (0.51 ml, 3.65 mmol) in ethanol (30 ml) with an overnight reflux. The product was flash chromatographed on silica gel (10% ethyl acetate/hexane elution); 0.889 g (51%); NMR 8.13 (d, J=9 Hz, 2H), 7.38 (m, 2H), 7.30–7.15 (m, 3H), 6.83 (d, J=9 Hz, 2H), 3.93 (q, J=7 Hz, 1H), 3.42–3.28 (m, 3H), 2.05–1.56 (m, 9H), 1.32 (d, J=7 Hz, 3H), 0.99 (s, 9H), 0.25 (s, 6H); IR 2940, 2840, 1600, 1390–1290 (br), 910.

EXAMPLE 14

Mixture of (1R*,2S*)- and (1S*,2S*)-1-(4-(tert-Butyldimethylsilyloxy)phenyl)-2-(3-phenylthio-8-azabicyclo[3.2.1]oct-8-yl)-1-propanol This product was prepared as in Example 2 with overnight stirring at ambient temperature from the product of the preceding Example (0.85 g, 1.77 mmol) and $LiAlH_4$ (0.153 g, 4.0 mmol) in tetrahydrofuran (24 ml). The product was isolated as a yellow oil (0.78 g, 91%) as a mixture of racemic title products.

EXAMPLE 15

(1S*,2S*)- and (1R*,2S*)-1-(4-Hydroxyphenyl)-2-(3-phenylthio-8-azabicyclo[3.2.1]oct-8-yl-1-propanol Title product of the preceding Example (0.78 g, 1.6 mmol) was desilylated according to the procedure of Example 3 with tetrabutylammonium fluoride (1.6 ml, 1.6 mmol; 1M in tetrahydrofuran) in a 5 minute reaction. The resulting mixture of racemates were separated by silica gel flash chromatography (50% ethyl acetate/hexane elution). (1S*,2S*)-Title product eluted first; 0.133 g; NMR (DMSO d6) 7.40–7.21 (m, 5H), 7.06 (d, J=8.5 Hz, 2H), 6.63 (d, J=8.0 Hz, 2H), 4.35 (d, J=5.0 Hz, 1H), 3.54–3.40 (m, 2H), 3.35–3.29 (m, 2H), 2.70–2.62 (br t, 1H), 2.50 (m, 1H), 1.80–1.54 (m, 6H), 0.63 (d, J=6.5 Hz, 3H).

Continued elution gave (1R*,2S*)-title product: 0.102 g; NMR 7.45–7.40 (m, 2H), 7.32–7.22 (m, 3H), 7.15 (d, 2H), 6.76 (d, 2H), 4.80 (d, 1H), 3.60–3.52 (m, 2H), 3.51–3.38 (m, 1H), 2.80–2.72 (m, 1H), 2.00–1.55 (m, 8H), 0.68 (d, 3H). This product (80 mg) was converted to its HCl salt by dissolving in 15 ml of ether, bubbling in dry HCl for 2 minutes and triturating the resulting oily solid with ether to yield 30 mg as a white solid.

EXAMPLE 16

2-(4-Benzyl-4-hydroxypiperidino)-1-(4-(triisopropylsilyloxy)phenyl)-1-propanone

This product was prepared according to the procedures of Example 1 from 4-hydroxy-4-benzylpiperidine (2.72 g, 14.22 mmol), 4-triisopropylsilyloxy-alpha-bromopropiophenone (5.48 g, 14.22 mmol), and triethylamine (2.0 ml, 14.35 mmol) in ethanol (50 with a reflux time of 17 hours to give 4.92 g (70%) of present, chromatographed title product as an orange oil; NMR 8.01 (d, J=8.8 Hz, 2H), 7.31–7.22 (m, 3H), 7.18–7.15 (m, 2H), 6.87 (d, J=8.8 Hz, 2H), 4.03 (q, J=6.7 Hz, 1H), 2.72 (s, 2H), 2.68–2.57 (m, 3H), 2.45 (dt, 1H), 1.78–1.42 (m, 4H), 1.40–1.25 (m, 7H), 1.10 (d, 7 Hz, 18H).

EXAMPLE 17

(1S*,2S*)- and (1R*,2S*)-2-(4-Benzyl-4-hydroxypiperidino)-1-(4-(triisopropylsilyloxy)phenyl)-1-propanol Title product of the preceding Example (4.92 g, 9.33 mmol) was dissolved in ethanol (100 ml) and NaBH4(0.38 g, 10 mmol) was added all at once. After stirring overnight at ambient temperature, present (1S*,2S*)-title product was recovered by filtration, 2.11 g; NMR 7.46–7.17 (m, 7H), 6.84 (d, J=7 Hz, 2H), 4.18 (d, J=11 Hz, 1H), 2.86 (br t, 1H), 2.77 (s, 2H), 2.70–2.42 (m, 4H), 1.89–1.55 (m, 6H), 1.30–1.13 (m, 3H), 1.10 (d, J=8.6 Hz, 18H), 0.75 (d, J=6 Hz, 3H).

The filtrate was concentrated and the residue dissolved in ethyl acetate, extracted with water (2x) and brine, dried (CaSO4), concentrated to 2.33 g of a light yellow solid, and flash chromatographed on silica gel (2×6 inches, ethyl acetate/hexane gradient elution) to give first 1.4 g more of (1S*,2S*)-product, followed by 0.46 g of (1R*,2S*)-product; NMR 7.33–7.11 (m, 7H), 6.82 (d, J=8.6 Hz, 2H), 4.77 (d, J=4 Hz, 1H), 2.80–2.39 (m, 5H), 1.88–1.43 (m, 6H), 1.31–1.13 (m, 8H), 1.08 (d, J=6.7 Hz, 18H), 0.84 (d, J=6.9 Hz, 3H).

EXAMPLE 18

(1R*,2S*)-2-(4-Benzyl-4-hydroxypiperidino)-1-(4-hydroxyphenyl)-1-propanol

By the method of Example 3, using ethyl acetate/hexane gradient elution in chromatography, (1R*,2S*)-title product of the preceding Example (0.46 g, 0.92 mmol) was converted to 0.24 g (74%) of present title product as a monohydrate; mp 173°–174° C.; NMR (DMSO d6 with D2O added) 7.21–7.12 (m, 5H), 7.04 (d, J=7.6 Hz, 2H), 6.64 (d, J=8.6 Hz, 2H), 4.64 (d, J=8.6 Hz, 1H), 2.59 (s, 2H), 2.59–2.49 (m, 5H—partially under NMR solvent) 1.50–1.31 (m, 4H), 0.82 (d, J=7 Hz, 3H). Anal. C 70.26, H 7.96, N 3.85; calcd. for monohydrate, C 70.17, H 8.13, N 3.90.

EXAMPLE 19

2-(4-Benzyl-4-hydroxypiperidino)-1-(4-fluoro-phenyl)-1-propanone

Title product, prepared as in Example 10 in 80% yield, was recrystallized from ether, mp 119.5°–120° C.; Anal. C 73.41, H 7.08, N 4.03, calcd. C 73.87, M 7.09, N 4.10.

EXAMPLE 20

(1S*,2S*)- and (1R*,2S*)-2-(4-Benzyl-4-hydroxypiperidino)-1-(4-fluorophenyl)-1-propanol Title products, prepared as in Example 17, were separated by flash chromatography on silica gel (ethyl acetate-hexane then methanol-ethyl acetate gradient). The 1S*,2S* product eluted first in 84% yield as a solid which was recrystallized from ethanol/ether, mp 53.5°–154.5° C. Anal. C 73.53, H 7.67, N 4.08, calcd. C 3.44, H 7.63, N 4.08.

The 1R*,2S* product, eluted second in 15% yield, was recrystallized from ethanol/ether, mp 145°–146° C.; Anal. C 73.18, H 7.59, N 4.06, calcd. C 73.44, H 7.63, N 4.08.

EXAMPLE 21

2-(3-Phenylmethylene-8-azabicyclo[3.2.1]oct-8-yl)-1-4-benzyloxyphenyl)-1-propanone Title product, prepared following the procedure of Example 1 from 4-benzyloxy-alpha-bromopropiophenone, was obtained in 40–60% yield after silica gel flash chromatography; NMR 8.34 (d, 2H), 7.56–7.45 (m, 7H), 7.20 (d, 3H), 7.03 (d, 2H), 6.36 (s, 1H), 5.14 (s, 2H), 4.13 (q, 1H), 3.56–3.30 (m, 2H), 2.81 (t, 1H), 2.70–2.40 (m, 2H), 2.10–1.76 (m, 3H), 1.66 (m, 1H), 1.45 (d, 3H).

EXAMPLE 22

(1S*,2S*)-2-(3-Phenylmethylene-8-azabicyclo[3.2.1]oct-8-yl)-1-(4-benzyloxyphenyl)-1-propanol Title product, prepared following the procedure of Example 3 with a 1.25 hour reaction time, was obtained in pure form by flash chromatography on silica gel, mp 145°–148° C.; Anal. C 81.69, H 7.46, N 3.02, calcd. C 81.97, H 7.57, N 3.19.

EXAMPLE 23

(1S*,2S*)-2-(3-Benzyl-8-azabicyclo[3.2.1]oct-8-yl)-1-(4-hydroxyphenyl)-1-propanol Title product of the preceding Example (0.23 g, 0.523 mmol) was dissolved in tetrahydrofuran (20 ml) and chilled to −78° C. Ammonia (30 ml) was condensed into the solution. Sodium (0.06 g, 2.6 mmol) was added in three portions and a blue solution gradually formed. After 10 minutes the reaction was quenched with excess ammonium chloride and the mixture was allowed to warm to ambient temperature with evaporation of the ammonia. The residual mixture was concentrated, and the residue extracted with ethyl acetate. Filtration and concentration left 0.24 g of an oily solid which was flash chromatographed on silica gel (6×1 inch ethyl acetate/hexane gradient elution followed by methanol flushing). This gave first recovered starting material followed by product (0.071 g). The product was further purified by recrystallization (ethyl acetate/hexane). A portion was spilled during this process but 0.005 g of white solid product was obtained as a 1:3 mixture of epimers of the benzyl group; NMR 7.30–7.10 (m, 7H), 6.72 (J=8.5 Hz) and 6.71 (J=8.6 Hz) (pair of overlapping d, total 2H), 4.11 (d, J=8.6 Hz, 1H), 3.45 (s, 1H), 3.31 and 3.24 (pair of s, 1H), 2.73 (J=7.3 Hz) and 2.48 (J=7.2 Hz) (pair of d, 2H), 2.61 (quintet, J=7.6 Hz, 1H), 2.11 (m, 1H), 1.86–1.17 (m, 10H), 0.81 (d, J=6.7 Hz, 3H). HRMS 352.2276, calcd. for MH+ 352. 2278.

EXAMPLE 24

2-(4-Benzyl-4-hydroxypiperidino)-1-(4-chlorophenyl)-1-propanone

Title product, prepared from 4-chloro-alpha-bromopropiophenone, following the procedure of Example 10 in 72% yield, was purified by flash chromatography on silica gel and recrystallized from ether, mp 135.5°–136° C.; Anal. C 70.11, H 6.70, N 3.85, calcd. C 70.48, H 6.76, N 3.91.

EXAMPLE 25

(1S*,2S*)- and (1R*,2S*)-2-(4-Benzyl-4-hydroxypiperidino)-1-(4-chlorophenyl)-1-propanol Title products, prepared following the procedure of Example 17, were separated by the same chromatographic procedure. The 1S*,2S* product was obtained 70% yield, mp 159.5°–160.5° C. (ethanol/ether); Anal. C 70.13, H 7.50, N 3.91, calcd. C 70.08, H 7.28, N 3.89.

The 1R*,2S* product was obtained in 7% yield, mp 150.5°–151.5° C. (ethanol/ether); Anal. C 69.62, H 7.38, N 3.92, calcd. C 70.08, H 7.28, N 3.89.

EXAMPLE 26

2-(4-Benzyl-4-hydroxypiperidino)-1-(4-chlorophenyl)-1-ethanone

Title product was prepared following the procedure of Example 10 from 4-chloro-alpha-bromoacetophenone in 76% yield; NMR 7.93 (d, J=8.5 Hz, 2H), 7.39 (d, J=8.6 Hz, 2H), 7.31–7.16 (m, 5H), 3.74 (s, 2H), 2.74 (s, 2H), 2.73–2.71 (m, 2H), 2.43 (dt, J=11.5, 2.4 Hz, 2H), 1.80 (dt, J=12.7, 4.3 Hz, 2H), 1.50 (br d, J=13.8 Hz, 2H).

EXAMPLE 27

2-(4-Benzyl-4-hydroxypiperidino)-1-(4-chlorophenyl)ethanol

Title product, prepared from 4-chloro-alpha-broraoacetophenone following the procedure of Example 17 in 83% yield, was recrystallized from ethanol/ether, mp 151°–152° C.; NMR 7.34–7.18 (m, 9H), 4.67 (dd, J=10.5, 3.5 Hz, 1H), 4.18 (br s, 1H), 2.89–2.86 (m, 1H), 2.76 (s, 1H), 2.68–2.47 (m, 3H), 2.41–2.31 (m, 2H), 1.73 (dq, J=13.3, 4.4 Hz, 2H), 1.58–1.50 (m, 2H), 1.24 (s, 1H).

EXAMPLE 28

2-(4-Benzyl-4-hydroxypiperidino)-1-(4-fluorophenyl)-1-ethanone

Title product was prepared following the procedure of Example 10 in 59% yield from 4-fluoro-alpha-bromoacetophenone; NMR 8.05–7.99 (m, 2H), 7.33–7.04 (m, 7H), 3.76 (s, 2H), 2.83–2.71 (m, 4H), 2.43 (dt, J=11.5, 2.1 Hz, 2H), 1.82 (dt, J=12.7, 4.3 Hz, 3H), 1.51 (br d, J=11.5 Hz, 2H).

EXAMPLE 29

2-(4-Benzyl-4-hydroxypiperidino)-1-(4-fluorophenyl)-1-ethanol

Title product, prepared following the procedure of Example 17 in 85% yield, was recrystallized from ethanol/ether, mp 144.5°–146° C.; NMR 7.35–7.25 (m, 5H), 7.19 (d, J=6.4 Hz, 2H), 7.01 (t, J=8.7 Hz, 2H), 4.67 (dd, J=10.5, 3.5 Hz, 1H), 4.18 (br s, 1H), 2.88 (br d, J=11.2 Hz, 1H), 2.76 (s, 2H), 2.68–2.31 (m, 5H), 1.81–1.66 (m, 2H), 1.58–1.50 (m, 2H), 1.28 (s, 1H).

EXAMPLE 30

Endo-1-(4-(Triisopropylsilyoxy)phenyl)-2-(3′-phenylspiro[8-azabicyclo[3.2.1]octane-3,2′-oxirane]-8-yl)-1-propanone Title product of Preparation 13 below (0.72 g, 3.34 mmol), title product of Preparation 10 below (1.29 g, 3.35 mmol), and potassium carbonate (0.93 g, 6.7 mmol) were combined in tetrahydrofuran (80 ml), refluxed for 30 hours, cooled and filtered through diatomaceous earth. The filtrate was concentrated and chromatographed on silica gel (ethyl acetate/hexane gradient elution) to give 0.77 g (44%) of title product as a mixture of diastereomers. The epoxide protons were observed at delta 3.65 and 3.60 ppm in the NMR spectrum.

The corresponding exo isomer was prepared in like manner from the other isomer of Preparation 13 in 37% yield. The epoxide protons in the mixture of diasteromeric products were observed at 3.80 and 3.86 ppm in the NMR spectrum.

EXAMPLE 31

Endo- and exo-(1S*,2S*) and (1R*,2S*)-1-(4-(Triisopropylsilyloxy)phenyl)-2-(3′-phenylspiro[8-azabicyclo[3.2.1]octane-3,2′-oxirane]-8-yl)-1-propanol A mixture of present endo title products was prepared from endo title product of the preceding Example in 82% yield by the procedure of Example 17. Flash chromatography gave pure, faster running (1S*, 2S*)-isomer; NMR 7.34–7.23 (m, 5H), 7.17 (d, J=8.5 Hz, 2H), 6.82 (d, J=8.5 Hz, 2H), 4.02 (d, J=8 Hz, 1H), 3.65 (s, 1H), 3.45 (br s, 1H), 3.28 (br s, 1H), 2.65 (quintet, J=7.2 Hz, 1H), 2.54 (dd, J=13.8, 3.2 Hz, 1H), 2.15 (q, J=8.6 Hz, 2H), 1.93–1.72 (m, 4H), 1.40 (d, J=13.8 Hz, 2H). Slower running (1R*,2S*)-isomer, which shows a characteristic NMR signal at 4.81 ppm (br s, 1H) was obtained as a mixture with the (1S*,2S*)-isomer.

The corresponding exo isomers were prepared in like manner from the exo-isomer of the preceding Example in 82% yield as a 3:1 mixture of (1S*,2S*) and (1R*,2S*) isomers. The epoxide protons were seen at 3.86 and 3.82 ppm in the NMR spectrum.

EXAMPLE 32

Endo-(1S*,2S*)-1-(4-Hydroxyphenyl)-2-(3′-phenylspiro[8-azabicyclo-[3.2.1]octane-3,2′-oxirane]-8-yl)-1-propanol By the method of Example 3, endo-(1S*,2S*)-title product of the preceding Example was converted to present title product in 62% yield; mp 204.5°–205° C. (chloroform/hexane); NMR 7.32–7.25 (m, 5H), 7.17 (d, J=8.4 Hz, 2H), 6.73 (d, J=6.6 Hz, 2H), 5.25 (br s, 1H), 4.01 (d, J=8.2 Hz, 1H), 3.66 (s, 1H), 3.47 (br s, 1H), 3.31 (br s, 1H), 2.65–2.54 (m, 2H), 2.16 (d, J=8 Hz, 2H), 1.89–1.73 (m, 3H), 1.44 (br d, J=13.9 Hz, 1H), 1.24 (br d, J=14 Hz, 1H), 0.83 (d, J=6.7 Hz, 3H).

EXAMPLE 33

Endo-(1S*,2S*)-2-(3-Benzyl-3-hydroxy-8-azabicyclo[3.2.1]oct-8-yl)-1-(4-(triisopropylsilyloxy)phenyl)-1-propanol The endo-(1S*,2S*)/(1R*,2S*) mixture of Example 31 (0.19 g, 0.36 mmol) was dissolved in tetrahydrofuran (20 ml) and chilled to −78° C. Ammonia (30 ml) was condensed into the solution and sodium metal (0.08 g) was added in small chunks over 1 hour. At this time the mixture turned deep blue. The reaction was stirred 10 minutes longer, then quenched with solid NH4Cl. The ammonia was allowed to evaporate, the residual mixture was partitioned between ethyl acetate and water, and the aqueous layer was extracted with fresh ethyl acetate. The combined organic layers were washed with brine, dried over CaSO4 and concentrated to give 0.18 g (95%) of a light yellow oil, which was purified by flash chromatography on silica gel (ethyl acetate/hexane gradient elution) to give 0.1 g of colorless oil which was the (1S*,2S*)-title product; NMR 7.33–7.25 (m, 3H), 7.18 (d, J=8.3 Hz, 4H), 6.84 (d, J=8.4 Hz, 2H), 4.09 (d, J=7.5 Hz, 1H), 3.42 (br s, 1H), 3.13 (br s, 1H), 2.70–2.58 (m, 3H), 2.11–1.91 (m, 4H), 1.73–1.51 (m, 4H), 1.30–1.16 (m, 5H), 1.09 (d, J=6.9 Hz, 18H), 0.86 (d, J=6.7Mr, 3H).

EXAMPLE 34

Endo-(1S*,2S*)-2-(3-Benzyl-3-hydroxy-8-azabicyclo[3.2.1]oct-8-yl)-1-(4-hydroxyphenyl)-1-propanol By the procedure of Example 3, title product of the preceding Example was converted to present title product in 38% yield after flash chromatography and recrystallization from ethyl acetate/hexane; mp 162°–163° C.; $^{13}$C-NMR 156.97, 138.80, 135.86, 131.73, 129.11, 128.70, 127.07, 115.58, 76.09, 71.74, 64.64, 62.36, 54.62, 52.97, 45.82, 45.68, 29.28, 28.85, 14.50.

By the procedure of the preceding Example, the title product of Example 32 is converted to the same product.

EXAMPLE 35

Exo-(1S*,2S*)- and (1R*,2S*)-1-(4-hydroxyphenyl)-2-(3'-phenylspiro[8-azabicyclo[3.2.1]octane-3,2'-oxirane]-8-yl)-8-propanol By the procedure of Example 3, the exo-(1S*,2S*)/(1R*,2S*) mixture of Example 31 was converted to a mixture of present title products in 93% yield. The (1S*,2S*) isomer was separated by flash chromatography and recrystallized from ether/hexane, mp 115°–117° C. The (1R*,1S*) isomer, obtained as a minor component (about 25%) in later fractions of the chromatography, was also recrystallized from ether/hexane, mp 107°–110° C.

EXAMPLE 36

1-(4-(Triisopropylsilyloxy)phenyl)-2-(4-hydroxy-4-phenylpiperidino)-1-propanone

By the procedure of Example 1, 4-hydroxy-4-phenylpiperidine was converted to present title product in 37% yield as a clear oil; NMR 8.03 (d, J=8.5 Hz, 2H), 7.47 (d, J=8 Hz, 2H), 7.33 (t, J=7.5 Hz, 2H), 7.26–7.24 (m, 1H), 6.89 (d, J=8.5 Hz, 2H), 4.08 (q, J=7.5 Hz, 1H), 2.90–2.60 (m, 2H), 2.25–2.10 (m, 2H), 1.85–1.75 (m, 2H), 1.65–1.55 (m, 2H), 1.32–1.22 (m, 6H), 1.10 (d, J=7 Hz, 18).

EXAMPLE 37

(1S*,2S*)-1-(4-Triisopropylsilyloxy)phenyl)-2-(4-hydroxy-4-phenylpiperidino)-1-propanol By the procedure of Example 17, title product of the preceding Example was converted to present title product in 87% yield; mp 148°–151° C.; NMR 7.52 (d, J=7 Hz, 2H), 7.38 (t, J=7 Hz, 2H), 7.30–7.25 (m, 1H), 7.19 (d, J=8.5 Hz, 2H), 6.84 (d, J=8.5 Hz, 2H), 4.23 (d, J=9.5 Hz, 1H), 3.13–3.02 (m, 1H), 2.80–2.58 (m, 3H), 2.30–2.08 (m, 2H), 1.90–1.78 (m, 2H), 1.29–1.17 (m, 3H), 1.09 (d, J=7 Hz, 18H), 0.79 (d, J=6.5 Hz, 3H).

EXAMPLE 38

(1S*,2S*)-1-(4-Hydroxyphenyl)-2-(4-hydroxy-4-phenylpiperidino)-1-propanol

Title product, prepared following the procedure of Example 3 from title product of the preceding Example in 65% yield, was recrystallized from ethanol; mp 202°–204° C.; Anal. C 71.95, H 8.09, N 4.26, calcd. for 0.5 C2H5OH, C 71.97, H 8.05, N 4.00.

EXAMPLES 39–76

Using the methods of the preceding Examples, the following additional compounds were prepared, specifying yield to purified material in the final step:

39. 2-(4-Benzyl-4-hydroxypiperidino)-1-(4-hydroxyphenyl)ethanol; 42%; mp 98°–99° C. (from ethanol).

40. (1S*,2S*)-2-(4-Benzyl-4-hydroxypiperidino)-1-(4-methoxyphenyl)-1-propanol; 36%; mp 145.5°–146° C. (from ethanol/ether).

41. (1S*,2S*)-2-(4-Benzyl-4-hydroxypiperidino)-1-(4-hydroxyphenyl)-1-pentanol; 55%; mp 158°–159° C. (from ethanol/ether).

42. (1R*,2S*)-2-(4-Benzyl-4-hydroxpiperidino)-1-(4-hydroxyphenyl)-1-pentanol; 37%; mp 156°–157° C. (from ether).

43. (1S*,2S*)-2-(4-Benzyl-4-hydroxypiperidino)-1-(4-hydroxyphenyl)-1-butanol; 53%; mp 190°–191° C. (from ethanol).

44. (1S*,2S*)-2-(4-Benzyl-4-hydroxypiperidino)-1-(4-methoxyphenyl)-1-butanol; 61%; mp 143°–144° C. (purified by flash chromatography on silica gel using ethyl acetate/hexane gradient elution).

45. 2-(4-Benzyl-4-hydroxypiperidino)-1-(4-cyanophenyl)ethanol; 52%; mp 142°–143° C. (from ethanol/ether/hexane).

46. 2-(4-Benzyl-4-hydoxypiperidino)-1-(2-hydroxyphenyl)ethanol; 43%; mp 172°–173.5° C. (from ethanol).

47. 2-(4-Benzyl-3-hydroxypiperidino)-1-(3hydroxyphenyl)ethanol; 76%; mp 198°–199° C. (from ethanol).

48. 1-(4-Chlorophenyl)-2-(4-hydroxy-4-phenylpiperidino)ethanol; 63%; mp 155.5°–157° C. (from ethanol/ether).

49. (1S*,2S*)-2-(4-(4-chlorophenyl)-4-hydroxypiperidino)-1-(4-hydroxyphenyl)-1-propanol; 58%; mp 204°–206° C. (from ethyl acetate).

50. 2-(4-Hydroxy-4-phenylpiperidino)-1-(2-thienyl)ethanol; 54%; mp 167°–168° C. (from ethanol).

51. (1S*,2S*)-Exo-1-(4-Hydroxyphenyl)-2-(3-(2-thienylthio)-8-azabicyclo[3.2.1]oct-8-yl)-1-propanol; 38%; mp 127.5°–129° C. (from ethyl acetate/hexane).

52. (1R*,2S*)-Exo-1-(4-Hydroxyphenyl)-2-(3-(2-thienylthio)-8-azabicyclo[3.2.1]oct-8-yl)-1-propanol; 19%; mp 141°–142.5° C. (from ethyl acetate).

53. (1S*,2S*)-Exo-2-(3-(4-chlorophenylthio)-8-azabicyclo[3.2.1]oct-8-yl)-1-(4-hydroxyphenyl)-1-propanol; 84%; mp 181°-182.5° C. (from ethyl acetate).

54. (1R*,2S*)-Exo-2-(3-(4-chlorophenylthio)-8-azabicyclo[3.2.1]oct-8-yl)-1-(4-hydroxyphenyl)-1-propanol; 94%; mp 154°-156° C. (from ethyl acetate/hexane).

55. (1S*,2S*)-Exo-1-(4-Hydroxyphenyl)-2-(3-(4-methoxyphenylthio)-8-azabicyclo[3.2.1]oct-8-yl)-1-propanol; 55%; mp 118°-119° C. (from ethyl acetate/hexane).

56. (1R*,2S*)-Exo-1-(4-Hydroxyphenyl)-2-(3-(4-methoxyphenylthio)-8-azabicyclo[3.2.1]oct-8-yl)-1-propanol; 37%; mp 72°-75° C. (flash chromatography on silica gel using ethyl acetate/hexane gradient elution and hexane trituration).

57. 1-(4-Trifluoromethylphenyl)-2-(4-hydroxy-4phenylpiperidino)ethanol; 34%; mp 152°-153° C. (from ethanol/ether).

58. 1-(4-Acetamidophenyl)-2-(4-hydroxy-4-phenylpiperidino)ethanol; 34%; mp 217.5°-218° C. (from ethanol).

59. (1S*,2S*)-1-(4-hydroxyphenyl)-2-[4-hydroxy-4-(2-phenylethyl)piperidino]-1-propanol; 51%; mp 200°-201° C. (from ethyl acetate).

60. (1S*,2S*)-1-(4-Hydroxyphenyl)-2-[4-hydroxy-4-(3-phenylpropyl)piperidino]-1-propanol; 46%; mp 200.5°-201° C. (from ethyl acetate).

61. (1S*,2S*)-2-[4-(4-Fluorophenyl)-4-hydroxypiperidino]-1-(4-hydroxyphenyl)-1-propanol; 37%; mp 197°-198° C. (from ethyl acetate).

62. 1-(4-Cyanophenyl)-2-(4-hydroxy-4-phenylpiperidino)ethanol; 51%; mp 140°-140.5° C. (from ethanol/ether).

63. (1S*,2S*)-1-(4-Hydroxyphenyl)-2-[4-hydroxy-4-(4-methylphenyl)piperidino]-1-propanol; 41%; mp 188°-189° C.

64. 1-(4-Carbamoylphenyl)-2-(4-hydroxy-4-phenylpiperidino)ethanol; 23% mp 213.5°-215° C. (from ethanol).

65. (1S*,2S*)-1-(4-Hydroxyphenyl)-2-(3-endohydroxy-3-phenyl-8-azabicyclo[3.2.1]octan-8-yl)-1-propanol; 60%; 216°-217° C. (from ethanol/ether).

66. (1S*,2S*)-1-(4-Fluorophenyl)-2-(4-hydroxy-4-phenylpiperidino)-1-propanol; 44%; mp 177°-179° C. (from ethanol).

67. (1R*, 2S*)-1-(4-Hydroxyphenyl)-2-(4-hydroxy-4-phenylpiperidino)-1-propanol; 25%; mp 152°-155° C. (from ethanol).

68. (1S*,2S*)-2-(4-Hydroxy-4-phenylpiperidino)-1-phenyl-1-propanol; 50%; mp 149°-152° C. (from ethyl acetate/hexane).

69. (1S*,2S*)-1-(4-Chlorophenyl)-2-(4-hydroxy-4-phenylpiperidino)-1-propanol; 38%; mp 192°-194° C. (from ethanol).

70. 1-(4-Aminophenyl)-2-(4-hydroxy-4-phenylpiperidino)ethanol; 47%; mp 156.5°-158° C. (from ethyl acetate/ether).

71. (1S*,2S*)-2-(3-Benzyl-3-hydroxypyrrolidino)-1-(4-hydroxyphenyl)-1-propanol; 71%; mp 134°-136° C.

72. (1S*,2S*)-1-(4-Hydroxyphenyl)-2-(3-hydroxy-3-phenylpyrrolidino)-1-propanol; 56%; mp 74°-78° C.

73. (1S*,2S*)-1-(4-Chlorophenyl)-2-[4-hydroxy-4-(2-phenylethyl)piperidino]-1-propanol; 33%; mp 152°-154° C. (from ethanol).

74. (1S*,2S*)-1-(4-Hydroxyphenyl)-2-[4-hydroxy-4-(4-phenylbutyl)piperidino]-1-propanol; 44%; mp 191°-192° C. (from ethanol).

75. 1-(4-Carboxyphenyl)-2-(4-hydroxy-4-phenylpiperidino)ethanol; 98%; mp 254.5°-255° C. (from $H_2O$).

76. 2-(4-Hydroxy-4-phenylpiperidino)-1-(methoxycarbonyl)phenyl]ethanol; 57%; mp 138.5°-139.5° C. (from ethanol/ether).

EXAMPLE 77

(R-1-(4-Chlorophenyl)-2-(4-hydroxy-4-phenylpiperidino)ethanol

4-Hydroxy-4-phenylpiperidine (177 mg, 1 mmol) was dissolved in dry tetrahydrofuran (13 mL) and chilled to −15° C. with stirring and under a nitrogen atmosphere. Butyllithium (0.8 ml, 2 mmol, 2.5N) was added dropwise over 3 minutes. (−)-R-1-(4-chlorophenyl)ethylene oxide [155 mg, 1 mmol; J. Am. Chem. Soc. 109, 7925 (1987); J. Org. Chem. 53, 2861 (1988)] was dissolved in I mL tetrahydrofuran and added to the cold reaction with a 1 mL rinse. The mixture was warmed to ambient temperature and finally refluxed overnight. The mixture was cooled to room temperature and quenched with solid $NaHCO_3$. The crude reaction was directly chromatographed on silica gel using on ethyl acetate-hexane gradient elution. The product containing fractions were carefully rechromatographed on silica gel with 50% ethyl acetate-hexane elution to give 112 mg (33%) of product as an oily foam. Trituration with ether-hexane gave 15.2 mg of cream colored product which had mp 110°-113° C.; $[alpha]_D = -18°$.

(S)-1-(4-(Chlorophenyl)-2-(4-hydroxy-4-phenylpiperidino)ethanol, having the same physical properties except for sign of rotation was prepared in the same manner from (+)-S-1-(4-chlorophenyl) ethylene oxide.

EXAMPLE 78

Enantiomeric (1S,2S)- and (1R,2R)-1-(4-Hydroxyphenyl)-2-(4-hydroxy-4-phenylpiperidino)-1-propanols (+)-Tartaric acid (300 mg, 2 mmol) was dissolved in 30 mL warm methanol. Racemic 1S*,2S*-1-(4-hydroxyphenyl)-2-(4-hydroxy-4-phenylpiperidinyl)propanol (655 mg, 2 mmol) was added all at once. With stirring and gentle warming a colorless homogeneous solution was obtained. Upon standing at ambient temperature 24 hours, 319 mg (66%) of a fluffy white precipitate was obtained. This product was recrystallized from methanol to give 263 mg of the (+)-tartrate salt of levorotatory title product as a white solid; mp 206.5°-207.5° C.; $[alpha]_D = -36.2°$ C. This salt (115 mg) was added to 50 ml of saturated $NaHCO_3$. Ethyl acetate (5 ml) and the mixture was vigorously stirred 30 minutes. The aqueous phase was repeatedly extracted with ethyl acetate. The organic layers were combined and washed with brine, dried over calcium sulfate, and concentrated. The tan residue was recrystallized from ethyl acetate-hexane to give 32 mg (39%) of white, levorotatory title product; mp 203°-204° C.; $[alpha]_D = -56.9°$. Anal. Calcd. for $C_{20}H_{25}NO_3$: C, 73.37; M, 7.70; N, 4.28. Found: C, 72.61; H, 7.45; N, 4.21.

The filtrate from the (+)-tartrate salt preparation above was treated with 100 ml saturated aqueous $NaHCO_3$ and extracted well with ethyl acetate. The combined organic extracts were washed with brine, dried over calcium sulfate and concentrated to give 380 mg of recovered starting material (partially resolved). This material was treated with (−)-tartaric acid (174 mg) in 30 mL of methanol as above. After standing for 24 hours, filtration gave 320 mg (66%) of product which was further recrystallized from methanol to produce 239 mg the (−)-tartrate salt of dextrorotatory title product; mp 206.5°–207.5° C.; [alpha]$_D$ = +33.9°. The latter was converted to dextrorotatory title product in the manner above in 49% yield; mp 204°–205° C.; [alpha]$_D$ = +58.4°. Anal. Found: C, 72.94; M, 7.64; N, 4.24.

EXAMPLE 79

(1S*,2S*)-1-(4-Hydroxyphenyl)-2-(1,2,3,6-tetrahydro-4-phenylpyrido)-1-propanol

By the methods of Examples 1, 2 and 3, 4-(triisopropylsilyloxy)-alpha-bromopropiophenone and 1,2,3,6-tetrahydro-4-phenylpyridine were converted to present title product in 14% yield in the last step; mp 208°–211° C. (dec.).

PREPARATION 1

8-(2,2,2-Trichloroethoxycarbonyl)-3-phenylmethylene-8-azabicyclo[3.2.1]octane

A solution of benzyltriphenylphosphonium chloride (13.26 g, 34.1 mmol) in tetrahydrofuran (400 ml) was chilled to −78° C. and butyl lithium (13.6 ml of 2.5M in hexanes, 34 mmol) was added. This resulted in a heterogeneous orange mixture which was stirred 5 minutes at −78° C. and then warmed to 0° C. The solution became nearly homogeneous red and N-2,2,2-trichloroethoxycarbonyltropinone (7.1 g, 23.3 mmol; Montzka al., Tetrahedron Letters, vol, 14, p. 1325, 1974) was added in tetrahydrofuran (20 ml with a 20 ml rinse). The reaction was refluxed 4 days, cooled, and filtered. Concentration of the filtrate left a viscous brown oil. Flash chromatography on silica gel (3×6 inches) using first hexane and then an ethylacetate/hexane gradient gave 7.87 g of white solid product (74%); mp 88°–89° C., ir (KBr) 3437, 2958, 1700, 1445, 1425, 1321, 1125, 711. Anal. C 54.89, H 4.82, N 3.77, calcd. C 54.49, H 4.84, N 3.74.

PREPARATION 2

3-Phenylmethylene-8-azabicyclo[3.2.1]octane

A mixture of title product of the preceding Preparation (1.0 g, 2.67 mmol), zinc dust (0.88, 13.46 mmol), and acetic acid (50 ml) was stirred overnight. The reaction was then heated at 70° C. for 22 hours, then cooled and concentrated. The residue was partitioned between ether/ethyl acetate and saturated NaHCO$_3$, and the mixture stirred 30 minutes and then filtered over diatomaceous earth. The aqueous phase was separated and further extracted with ethyl acetate (2x). The combined organic layers were washed with water and brine, dried (CaSO$_4$) and concentrated to leave 0.5 g of light yellow oil. Further purification was effected by taking the oil up in 10% HCl. This acid solution was extracted with ethyl acetate (2x). The acidic layer was neutralized over ice with sodium hydroxide and back extracted into ethyl acetate. This organic layer was dried (CaSO$_4$) and concentrated to leave 0.24 g (48%) of light yellow oil; NMR 7.24 (m, 2H), 7.13 (d, J=6.6 Hz, 3H), 6.28 (s, 1H), 3.52 (br d, J=28.2 Hz, 2H), 2.56 (t, J=15.4 Hz, 3H), 2.26 (d, J=14.7 Hz, 1H), 2.12 (d, J=13.9 Hz, 1H), 1.64 (m, 3H), 1.40 (m, 1H).

Alternatively, the product was converted to its HCl salt by treating an acetone solution with HCl gas.

PREPARATION 3

4-(tert-Butyldimethylsilyloxy)propiophenone

4-Hydroxypropiophenone (15 g, 100 mmol) and imidazole (17 g, 250 mmol) were dissolved in dimethylformamide (50 ml). tert-Butyldimethylsilyl chloride (19.6 g, 130 mmol) in dimethylformamide (40 ml) was added dropwise at ambient temperature. The mixture was stirred 18 hours, then diluted with water (300 ml) and extracted with ether (4×200 ml). The combined ether layers were washed with 1M LiCl and brine, dried (CaSO$_4$), concentrated to an oily solid, flash chromatographed on silica gel using 1:10 ethylacetate:hexane as eluant to yield 26 g of title product which was further purified by short path distillation to yield 23.2 g (88%) of purified title product as a hygroscopic white solid; mp 30°–31° C.; NMR 7.76 (d, J=Hz, 2H), 6.74 (d, J=Hz, 2H), 2.82 (q, J=Hz, 2H), 1.09 (t, J=Hz, 3H), 0.87 (s, 9H), 0.11 (s, 6H).

PREPARATION 4

4-(tert-Butyldimethylsilyloxy)-alpha-bromopropiophenone 4-(tert-Butyldimethylsilyloxy)propiophenone (20 g, 75.8 mmol) was dissolved in acetic acid (300 ml) and bromine (3.9 ml, 75.8 mmol in 30 ml of acetic acid) was added dropwise. The orange color of bromine persisted for about 1 minute and then the reaction rapidly decolorized as the bromine was added. The reaction was stirred 1 hour further, then concentrated and the residue flash chromatographed on silica gel (hexane elution) to give 7.12 g of oily product; NMR 7.92 (d, J=9 Hz, 2H), 6.86 (d, J=9 Hz, 2H), 5.22 (q, J=6.5 Hz, 1H), 1.85 (d, J=6.5 Hz, 3H), 0.96 (s, 9H), 0.22 (s, 6H). $^{13}$C NMR 76.73, 59.55, 40.47, 38.59, 37.68, 25.42.

PREPARATION 5

O-Methanesulfonyltropine

Tropine (14.2 g, 100 mmol) was dissolved in CH$_2$Cl$_2$ (210 ml) and triethylamine (23 ml, 160 mmol) was added. Methanesulfonyl chloride (9.3 ml, 120 mmol) was added rapidly dropwise which caused the methylene chloride solution to reflux gently. The mixture was stirred one hour further; then extracted with cold 0.5 molar sodium hydroxide, water, and brine, dried by filtration through phase separating paper and concentrated to yield 13.8 g (65%) of title product as a yellow solid; NMR 4.88 (t, J=5 Hz, 1H), 3.10–3.05 (m, 2H), 2.94 (s, 3H), 2.22 (s, 3H), 2.20–2.10 (m, 2H), 2.02–1.88 (m, 6H).

PREPARATION 6

3-Phenylthio-8-methyl-8-azabicyclo[3.2.1]octane

NaIl (60% in oil; 2.77 g, 69 mmol) was washed with hexane (3x) and then suspended in tetrahydrofuran (300 ml). Thiophenol (6.5 ml, 63 mmol) in tetrahydrofuran (25 ml) was added dropwise over 5 minutes. The milky white suspension which formed, with hydrogen evolution, was stirred 10 minutes and then O-methanesulfonyltropine (13.8 g, 63 mmol in 25 ml of tetrahydrofuran) was added all at once. The mixture was refluxed overnight, cooled and filtered through diatomaceous earth with ether wash. The filtrate was diluted with ethyl acetate and washed with cold 1M NaOH, water, and brine, dried (CaSO$_4$) and concentrated to yield 11.48 g (78%) of title product as a yellow solid; NMR 7.50–7.18 (m, 5H), 3.32–3.21 (m, 1H), 3.15–3.09 (m, 2H), 2.25 (s, 3H), 2.02–1.94 (m, 2H), 1.79–1.72 (m, 4H), 1.60–1.51 (m, 2H); $^{13}$C NMR 134.8, 132.3, 128.8, 126.9, 61.16, 39.21, 38.38, 37.72, 26.42.

PREPARATION 7

3-Phenylthio-8-(2,2,2-trichloroethoxycarbonyl)-8-azabicyclo[3.2.1]octane

Title product of the preceding Preparation (11.48 g, 49.3 mmol) and K$_2$CO$_3$ (0.75 g, 5.4 mmol) were mixed with benzene (200 ml) and 2,2,2-trichloroethyl chloroformate (7.5 ml, 54.4 mmol) was added rapidly. The reaction was refluxed 2 hours, cooled, filtered, and concentrated. The orange oily residue was dissolved in CH$_2$Cl$_2$, washed with saturated NaHCO$_3$ and then brine, dried (CaSO$_4$) and concentrated. The residue was purified by flash chromatography on silica gel (hexane and then 5% ethyl acetate/hexane elution) to give first unreacted thiophenol from the previous reaction and then title product as a yellow oil (13 g, 67%); NMR 7.42–7.23 (m, 5H), 4.72 (AB q, J=12 Hz, 2H), 4.35–4.30 (m, 4H), 2.73 (heptet, J=6 Hz, 1H), 2.05–1.68M, 6H). The oil was solidified by trituration with hexane; mp 83°–84.5° C.; Anal. C 48.47, H 4.58, N 3.49, calcd. C 48.68, H 4.60, N 3.55.

PREPARATION 8

3-Phenylthio-8-azabicyclo[3.2.1]octane

Title product of the preceding Preparation (13.0 g, 33 mmol) was dissolved in acetic acid (400 ml) and zinc dust (11 g, 168 mmol) was added. The mixture was heated to 100° C. overnight, then concentrated and the residue partitioned between CH$_2$Cl$_2$ and saturated NaHCO$_3$. The resulting emulsion was cleared by filtration through diatomaceous earth. The phases were separated and the organic layer was dried through phase separating filter paper and concentrated to yield 6.1 g (84%) of title product as a yellow oil which solidified on standing; NMR 7.38–7.36 (m, 2H), 7.29–7.20 (m, 3H), 3.52 (s, 2H), 3.36 (heptet, J=6 Hz, 1H), 1.94–1.54 (m, 8H); $^{13}$C NMR 134.0, 132.43, 128.83, 127.06, 54.93, 40.81, 39.01, 28.98.

PREPARATION 9

4-(Triisopropylsilyloxy)propiophenone

By the method of Preparation 3, 4-hydroxypropiophenone and triisopropylsilyl chloride were converted to present title product as a clear oil in 100% yield; NMR 7.87 (d, J=8.5 Hz, 2H), 6.89 (d, J=8.5 Hz, 2H), 2.94 (q, J=7 Hz, 2H), 1.32–1.15 (m, 3H), 1.20 (t, J=7 Hz, 3H), 1.09 (d, J=7 Hz, 18H).

PREPARATION 10

4-(Triisopropylsilyloxy)-alpha-bromopropiophenone

Title product of the preceding Preparation (60.63 g, 198 mmol) was dissolved in CCl$_4$ (1100 ml) and a solution of bromine (11 ml, 210 mmol in 60 ml CCl$_4$) added dropwise. After a portion of the bromine solution was added without any noticeable decoloration after 15 minutes, acetic acid (1.0 ml) was added in two portions. The solution decolorized within 20 minutes and the addition was completed fairly rapidly. The mixture was stirred 15 minutes more; then the volatile HBr was partially removed with the aid of a nitrogen stream. The reaction was poured onto water (600 ml) and the phases were separated. The organic layer was washed with water, saturated NaHCO$_3$, water, and brine, dried (CaSO$_4$), and concentrated to leave 76.2 g (100%) of present title produced as a clear yellow oil; NMR 7.94 (d, J=9 Hz, 2H), 6.91 (d, J=9 Hz, 2H), 5.24 (q, J=6.5 Hz, 1H), 1.87 (d, J=6.5 Hz, 2H), 1.33–1.17 (m, 3H), 1.10 (d, J=7 Hz, 18H).

PREPARATION 11

4-Fluoro-alpha-bromopropiophenone

Title product, prepared as in Preparation 4 in 86% yield after distillation, was recrystallized from ethanol to afford a white crystalline solid; mp 33°–34° C. Anal. C 46.67, H 3.38, calcd. C 46.78, H 3.49.

PREPARATION 12

4-Chloro-alpha-bromopropiophenone

The product, prepared following the procedure of Preparation 10 in 98% yield, was recrystallized from ethanol, mp 78°–79° C.; Anal. C 43.74, H 3.17, calcd. C 43.67, H 3.26.

PREPARATION 13

Endo- and Exo-8-(2,2,2-Trichloroethoxycarbonyl)-3′phenyl-spiro[8-azabicyclo[3.2.1]octane-3,2′-oxirane]

The title product of Preparation 2 (5.0 g, mmol) was dissolved in CH$_2$Cl$_{12}$ (80 ml) and m-chloroperbenzoic acid (2.71 g, 13.35 mmol, purity) added. After stirring at ambient temperature overnight, the mixture was extracted with saturated NaHCO$_3$, then with water and brine, dried through phase separating paper, and concentrated to give 5.3 g of a glassy yellow oil which was chromatographed on silica gel (ethyl acetate/hexane gradient elution). Recovered starting material was eluted first followed by a fast moving endo epoxide product (2.23 g, 42.8%); mp 78°–79° C.; Anal. C 52.75, H 4.44, N 3.20, calcd. C 52.26, H 4.64, N 3.59; and finally by a slow moving exo epoxide product (2.32 g, 44.5%); mp 107°–108° C.; Anal. C 52.34, H 4.40, N 3.54, calcd. as for endo isomer.

PREPARATION 14

Endo- and exo-3′-Phenylspiro[8-azabicyclo[3.2.1]-octane-3,2′-oxirane]

The fast moving endo product of the preceding Example (1.55 g, 3.97 mmol) was dissolved in tetrahydrofuran (30 ml) and zinc powder (9.3 g, 142 mmol) and 1 molar monopotassium phosphate (10 ml) were added. After stirring overnight, the mixture was diluted with water (10 ml), the pH adjusted to 10–11 with NaCO$_3$ and filtered over diatomaceous earth with ethyl acetate and water wash. The aqueous layer in the combined filtrate and washes was separated and washed with fresh ethyl acetate. The combined organic layers were washed with brine, dried (CaSO$_4$) and stripped to yield 0.85 g (100%) of endo-title product as a yellow oil. Short path distillation (110°–115° C. bath temperature, 0.5 mm) gave endo title product as a clear colorless oil; NMR 7.34–7.23 (m, 5H), 3.63–3.60 (m, 2H), 3.55 (m, 1H), 2.36 (dd, J=14.1, 3.5 Hz, 1H), 2.17–2.12 (m, 2H), 1 . 83–1.81 (m, 2H), 1.70–1.61 (m, 2H), 1.42 (dt, J=11.9, 2.2 Hz, 1H), 1.18 (dt, J=14.5, 2.3 Hz, 1H). HRMS 215.1301, calcd. 215.1308.

By the same method, the slow moving isomer of the preceding Preparation was converted to the corresponding exo isomer in 96% yield, purified by short path distillation (110°–125° C. bath temperature, 0.8 mm); mp 114.5°–116° C. Anal. C 77.97, H 8.05, N 6.44, calcd. C 78.10, H 7.96, N 6.51.

I claim:

1. A compound of the formula:

(II)

wherein D is

R is H, $(C_1-C_6)$alkyl, $(C_2-C_6)$alkenyl or $(C_2-C_6)$alkynyl;

Q is S or CH=CH;

X is hydrogen, $(C_1-C_6)$alkyl, halo, $OR^1$, $OCOR^1$, $CO_2R^1$, $SR^1$, $NHR^1$, $NHCOR^1$, $CONH_2$ or CH;

$R^1$ is hydrogen or $(C_1-C_3)$alkyl;

$Y^2$ and $Y^3$ are taken separately, and $Y^2$ is OH and $Y^3$ is $Q^1$ is independently a value of Q as defined above;
$X^1$ is independently a value of X as defined above;
m is 0, 1, 2, 3 or 4; and
a pharmaceutically-acceptable acid addition salt thereof.

2. A compound of claim 1 wherein Q is CH=CH and X is substituted at the 4-position of the phenyl ring and is hydroxy, fluoro or chloro.

3. A compound of claim 2 wherein R is hydrogen, X is 4-fluoro or 4-chloro, and $Y^3$ is benzyl, 2-phenylethyl or 3-phenylpropyl.

4. A compound of claim 2 wherein R is methyl having 1S*,2S* relative stereochemistry:

5. A compound of claim 4 wherein X is 4-hydroxy and $Y^3$ is benzyl.

6. A compound of claim 4 wherein X is 4-fluoro and $Y^3$ is benzyl.

7. A compound of claim 4 wherein X is 4-chloro and $Y^3$ is benzyl.

8. A compound of claim 4 wherein X is 4-hydroxy and $Y^3$ is phenyl or 4-chlorophenyl.

9. A compound of claim 4 wherein X is 4-hydroxy and $Y^3$ is 2-phenylethyl.

10. A compound of claim 4 wherein X is 4-hydroxy and $Y^3$ is 3-phenylpropyl.

11. A pharmaceutical composition comprising a neuroprotective amount of a compound of claim 1 and a pharmaceutically acceptable carrier.

12. A method of treating stroke or a CNS degenerative disease in man which comprises treatment with a neuroprotective amount of a compound of claim 1.

* * * * *

UNITED STATES PATENT AND TRADEMARK OFFICE
CERTIFICATE OF CORRECTION

PATENT NO. : 5,338,754  Page 1 of 2
DATED : August 16, 1994
INVENTOR(S) : Bernard L. Chenard It is certified that error appears in the above-identified patent and that said Letters Patent is hereby corrected as shown below:

At column 2, lines 60-65, " 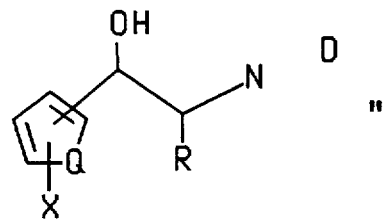 "

should read -- 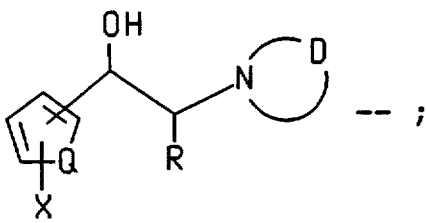 -- ;

At column 27, lines 10-12, " 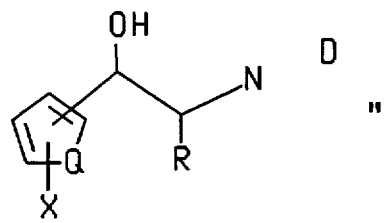 "

should read -- 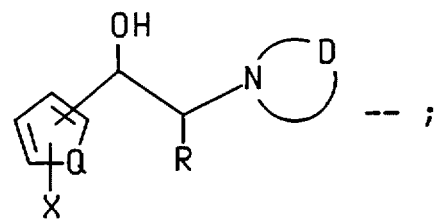 -- ;

UNITED STATES PATENT AND TRADEMARK OFFICE
CERTIFICATE OF CORRECTION

PATENT NO. : 5,338,754

DATED : August 16, 1994

INVENTOR(S) : Bernard L. Chenard

It is certified that error appears in the above-identified patent and that said Letters Patent is hereby corrected as shown below:

At column 27, lines 25-30, the following should be deleted " 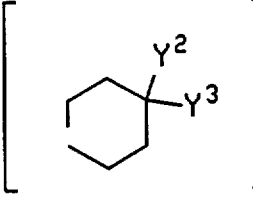 " .

Signed and Sealed this

Eighteenth Day of October, 1994

Attest:

BRUCE LEHMAN

Attesting Officer      Commissioner of Patents and Trademarks